(12) United States Patent
Crawford

(10) Patent No.: US 6,837,872 B2
(45) Date of Patent: Jan. 4, 2005

(54) NEEDLE HOLDER FOR USE WITH SAFETY NEEDLE ASSEMBLY

(75) Inventor: Jamieson William Maclean Crawford, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 105 days.

(21) Appl. No.: 10/173,948

(22) Filed: Jun. 17, 2002

(65) Prior Publication Data

US 2003/0208161 A1 Nov. 6, 2003

Related U.S. Application Data

(60) Provisional application No. 60/377,401, filed on May 2, 2002.

(51) Int. Cl.[7] .......................... A61M 5/00; A61M 5/178; A61B 5/00; B65D 81/00
(52) U.S. Cl. ................... 604/110; 604/164.01; 600/576
(58) Field of Search ............................ 604/110, 164.01, 604/164.08, 165.01, 165.02, 181, 182, 187, 192, 198; 600/576, 573, 577

(56) References Cited

U.S. PATENT DOCUMENTS

| | | | | |
|---|---|---|---|---|
| 4,887,998 A | * | 12/1989 | Martin et al. ............... | 604/110 |
| 5,009,642 A | * | 4/1991 | Sahi ........................... | 604/158 |
| 5,472,430 A | * | 12/1995 | Vaillancourt et al. ....... | 604/198 |
| 5,605,544 A | | 2/1997 | Tsao | |
| 5,718,239 A | * | 2/1998 | Newby et al. .............. | 600/576 |
| 5,893,845 A | * | 4/1999 | Newby et al. .............. | 604/198 |
| 5,951,520 A | * | 9/1999 | Burzynski et al. ...... | 604/170.01 |
| 6,146,337 A | | 11/2000 | Polidoro et al. | |
| 6,544,239 B2 | * | 4/2003 | Kinsey et al. .............. | 604/272 |
| 6,616,637 B2 | * | 9/2003 | Alexander et al. .......... | 604/192 |
| 6,629,956 B1 | * | 10/2003 | Polidoro et al. ........ | 604/164.01 |
| 2003/0060772 A1 | * | 3/2003 | Swenson ..................... | 604/183 |
| 2003/0208139 A1 | * | 11/2003 | Crawford .................... | 600/576 |
| 2003/0208160 A1 | * | 11/2003 | Crawford ............... | 604/164.08 |
| 2003/0208162 A1 | * | 11/2003 | Crawford .................... | 604/171 |

* cited by examiner

*Primary Examiner*—Nicholas D. Lucchesi
*Assistant Examiner*—Catherine S. Williams
(74) *Attorney, Agent, or Firm*—Gerald E. Hespos; Anthony J. Casella

(57) ABSTRACT

A needle holder for use with a needle assembly for blood collection is provided, and in particular, for use with a needle assembly including an activation mechanism adapted for axial displacement between a first position and a second position with respect to the needle assembly through engagement with a blood collection tube. The needle holder includes an outer body having a first end adapted for attachment to such a needle assembly and a second end having an internal opening therein. The needle holder further includes an inner body slidable within the outer body which includes a mechanism for axially displacing the activation mechanism between the first retracted position and the second activated position. The inner holder may be in the form of a tubular body which is axially slidable within the outer body, or may be in the form of an arm extending through a channel in the outer body, and including a tab for finger activation by a user.

9 Claims, 16 Drawing Sheets

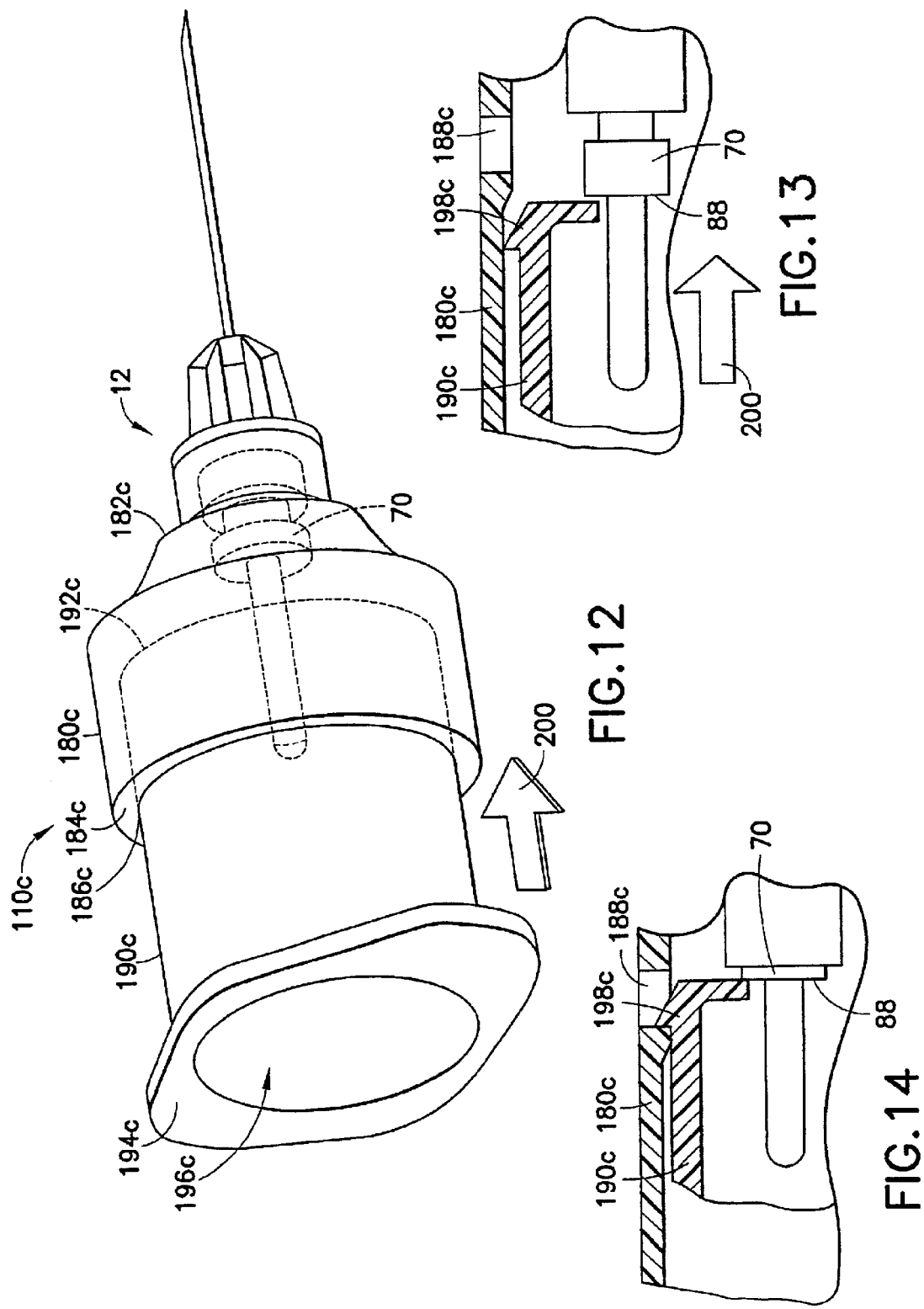

NEEDLE HOLDER FOR USE WITH SAFETY NEEDLE ASSEMBLY

RELATED APPLICATION

This application is a non-provisional of Appl. No. 60/377,401 filed on May 2, 2002.

BACKGROUND OF THE INVENTION

1. Field of the Invention

The present invention relates to a holder for use with dual end needle assemblies commonly used in blood collection procedures. More particularly, the present invention relates to a needle holder for use with a safety needle for blood collection from a patient and which includes a mechanism for activating the safety feature of the needle.

2. Description of Related Art

Disposable medical devices having piercing elements are typically used for administering a medication or withdrawing a fluid, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after usage. Thus, these blood collection systems allow repeated use of the relatively expensive holder upon replacement of the relatively inexpensive needle and/ or fluid collection tube. In addition to reducing the cost of collecting blood specimens, these blood collection systems also help minimize the production of hazardous medical waste.

A popular design configuration of previously available blood collection systems includes a double-ended needle assembly, an evacuated collection tube, and a holder for maintaining the needle assembly and the collection tube in fixed relation. The double-ended needle assembly, which is also referred to as a cannula, has a bore extending therethrough and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle extends forwardly of the holder for puncturing the vein of a patient. The opposite, second end of the needle extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal.

In addition to being capable of accommodating blood collection tubes, the holders of some fluid transfer systems are compatible with fluid containers having a fluid to be injected into a patient. Thus, such holders can be used to inject fluid into, as well as draw blood specimens from, a patient.

In order to reduce the risk of incurring an accidental needle-stick wound, protection of the used needle tip becomes important. With concern about infection and diseases of the blood, methods and devices to enclose the used disposable needle have become very important and in great demand. Many developments have taken place for protecting used needle tips. For example, U.S. Pat. No. 5,951,520 to Burzynski et al., discloses a self-blunting needle in which a rod or probe-like blunting member is disposed within the bore of a needle cannula having a puncture tip suitable for puncturing tissue. To prevent accidental needle-stick wounds from occurring after use of the device, the blunting member, which is retracted behind the puncture tip when the needle is injected into tissue, can be extended beyond the puncture tip of the needle cannula to effectively blunt the puncture tip by extending beyond it, so as to eliminate or at least greatly reduce the risk of accidental needle-stick punctures.

U.S. Pat. No. 5,810,775 to Shaw discloses a collection assembly which provides for retraction of the intravenous needle at the patient end of the assembly, and further discloses a hinged cap at the open end of the housing of the holder. After drawing a specimen into a collection tube, the collection tube is removed, and the hinged cap is closed over the opening of the holder, thereby activating the needle retraction and blocking access to the second end of the needle at the non-patient end. Activation of the hinged cap and the retraction mechanism requires substantial manipulation by the user and cannot be conveniently accomplished with a single hand, as is ideal for typical phlebotomy practice. Furthermore, the size of the device is relatively large, and the retraction mechanism for the needle can cause splattering of blood when the tip of a used needle is accelerated during retraction, thus potentially exposing health care workers to blood borne pathogens.

Accordingly, a need exists for a needle holder which can be used with a needle assembly which can be activated for safety blunting of the needle which is simple to manufacture, easy to operate, and does not occupy a significant amount of disposal space.

SUMMARY OF THE INVENTION

The present invention is directed to a needle holder for use in combination with a needle assembly which includes an activation mechanism adapted for axial displacement between a first position and a second position with respect to the needle assembly. The needle holder includes an outer body having a first end adapted for attachment to the needle assembly and a second end having an internal opening therein. The needle holder further includes an inner body slidable within the outer body and including a mechanism for axially displacing the activation mechanism between the first retracted position and the second activated position.

The inner body may be in the form of a tubular body concentric with the outer body. Such a tubular body includes a first end and an opposed second end, with the first end including the mechanism for axially displacing the activation mechanism of the needle assembly between the first retracted position and the second activated position, and the second end including an internal opening for accommodating a blood collection tube therein. Also, the first end of the tubular body of the inner holder may include an opening for accommodating a puncture tip of the needle assembly.

In a further embodiment, the outer body may include a channel extending axially along the outer body, and the inner body may include an arm which projects through the channel of the outer body and is axially slidable within the channel for axial displacement with respect to the outer body. As such, axial displacement of the arm causes the mechanism to axially displace the activation mechanism between the first retracted position and the second activated position. The arm desirably includes a locking mechanism for preventing axial displacement of the activation mechanism from the second activated position to the first retracted position. Also, a tab may be attached to the arm, with the tab adapted for finger activation by a user for causing axial displacement of the inner body within the outer body.

The present invention further includes a blood collection assembly including such a needle holder attached to a needle assembly. As well, the present invention includes a safety collection assembly including a safety needle assembly including an intravenous puncture tip, a non-patient puncture tip, and a blunting member having a blunted tip, said blunting member adapted for axial displacement with respect to the intravenous puncture tip between a first retracted position in which the intravenous puncture tip extends beyond the blunted tip and a second activated position in which the blunted tip extends beyond the intravenous puncture tip. The assembly further includes a needle holder attached to the needle assembly and includes an outer body having a first end adapted for attachment to the needle assembly and a second end having an internal opening therein, and an inner body slidable within the outer body and including a mechanism for engagement with the blunting member for axial displacement of the blunting member with respect to the intravenous puncture tip. The needle assembly may further include a second blunted tip adjacent the non-patient puncture tip, with the blunting member including a first end comprising the first blunted tip and a second opposing end comprising the non-patient puncture tip, and wherein axial displacement of the blunting member with respect to the intravenous puncture tip between the first retracted position and the second activated position also causes axial displacement of the non-patient puncture tip with respect to the second blunting tip between a first retracted position in which the non-patient puncture tip extends beyond the second blunted tip and a second activated position in which the second blunted tip extends beyond the non-patient puncture tip.

DESCRIPTION OF THE DRAWINGS

FIG. 12 is a perspective view of the needle assembly of the present invention shown in use with a further alternate needle holder.

FIG. 13 is a cross-sectional view of the needle assembly of the present invention shown in a retracted position in use with the needle holder of FIG. 12.

FIG. 14 is a cross-sectional view of the needle assembly of the present invention shown in an activated position in use with the needle holder of FIG. 12.

DETAILED DESCRIPTION

Figure 1:
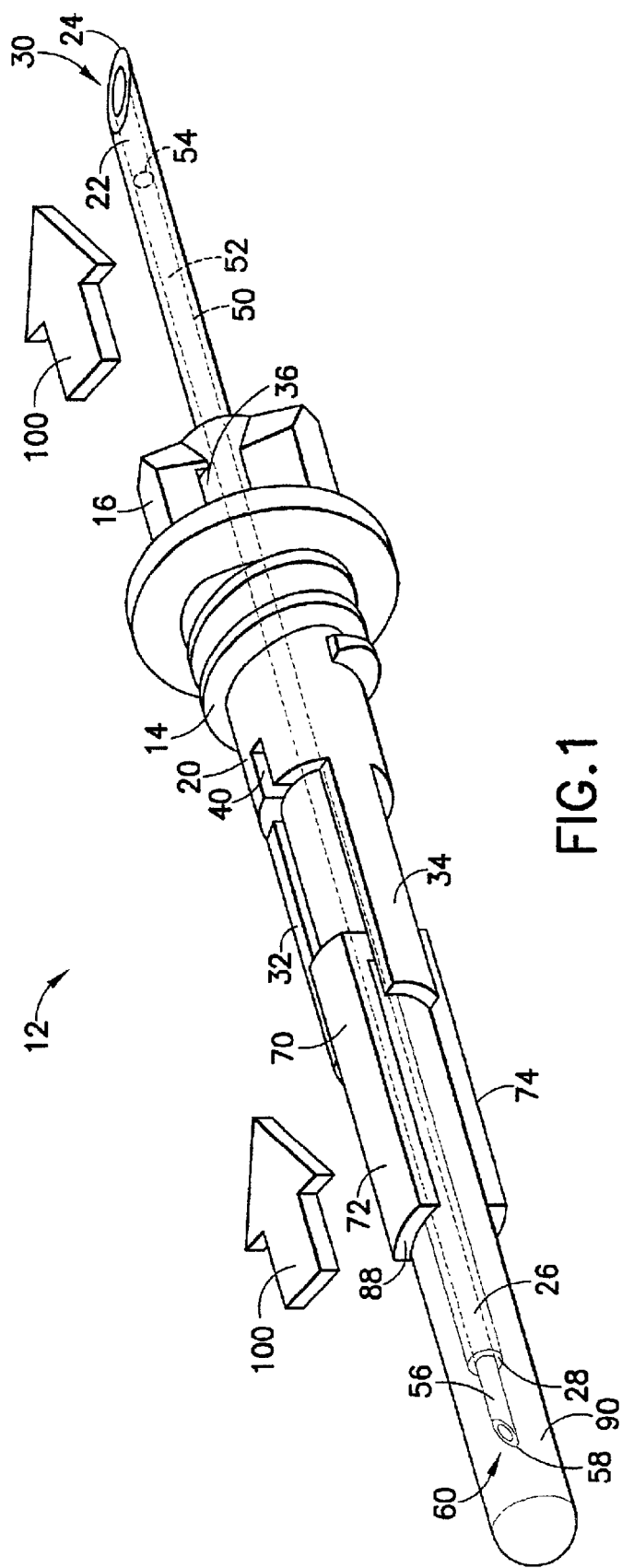
FIG. 1 is a perspective view of a dual blunting needle assembly in accordance with the present invention, shown in a retracted position for sampling.

While the present invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 to 4 illustrate a dual blunting needle assembly in accordance with the present invention and the related features. The needle assembly is in the form of a double-ended needle for use, for example, in combination with a needle holder for collecting blood samples. While the present invention is generally described in terms of a needle assembly, the present invention encompasses a needle assembly as well as a safety assembly which incorporates the needle assembly in combination with a needle holder, as will be discussed in more detail herein.

Needle assembly 12 of the present invention is shown generally at FIGS. 1–4. Needle assembly 12 defines a cannula assembly which is adapted for attachment to a separate needle holder, as is known in the art. As such, needle assembly 12 may be provided with means for attachment to a needle holder, such as attachment threads 14 which engage a threaded section of the needle holder. In this manner, needle assembly 12 can be provided as a disposable unit for use with a re-usable holder.

Needle assembly 12 includes a hub assembly 20 which defines a partial, generally tubular, housing for needle assembly 12. Hub assembly 20 includes a first external cannula 22 extending from a first end thereof, with an intravenous puncture tip 24 at the end of first external cannula 22. Hub assembly 20 further includes a second external cannula 26 extending from a second, opposing end thereof, with an external blunt tip 28 at the end of second external cannula 26. A central bore or internal lumen 30 extends through hub assembly 20 from intravenous puncture tip 24 to external blunt tip 28, providing for the passage of fluid therethrough, and to movably accommodate internal cannula 50, as will be discussed in more detail. External blunt tip 28 is blunted such that, under ordinary hand pressure, will not easily puncture human skin or other biological tissue. Intravenous puncture tip 24 is provided for insertion into the vein of a patient, for example, during a blood collection procedure. Accordingly, intravenous puncture tip 24 is desirably shaped to provide for ease of insertion and minimal discomfort during venipuncture, such as with a tapered pointed end, as is shown in the Figures and is known in the art.

Desirably, first external cannula 22 and second external cannula 26 are provided as separate members which are fixedly adhered to hub assembly 20, for example, using a medical grade adhesive. Desirably, first external cannula 22 is attached to hub assembly 20 through ferrule 46, which attaches directly to first external cannula 22 and fits within the first end of hub assembly 20.

As noted, hub assembly 20 includes second external cannula 26 extending from a second end thereof. As best seen in FIG. 1, hub assembly 20 includes arms 32 and 34, which extend axially along the length of needle assembly 12. Arms 32 and 34 are separate protrusions which define extensions of the generally tubular body of hub assembly 20. Arms 32 and 34 are separated, and therefore define channels therebetween for interfitting engagement with a carriage 70, as will be discussed in more detail herein.

Bridge member 42 extends between arms 32 and 34 at the second end of hub assembly 20. Such bridge member 42 further defines the general tubular body of hub assembly 20, and provides an area for attachment of second external cannula 26 to hub assembly 20. In particular, second external cannula 26 is fixedly adhered to hub assembly 20 within internal lumen 30 at bridge member 42, thereby providing second external cannula 26 as an extension of hub assembly 20. In an alternative embodiment, hub assembly 20 may have arm 32 and may not have arm 34. In a further embodiment, hub assembly 20 may consist of multiple components. These embodiments may aid assembly of the device.

Needle assembly 12 further includes internal cannula 50. Internal cannula 50 extends concentrically within internal lumen 30 of hub assembly 20. Internal cannula 50 includes first end 52, with an internal blunt tip 54 at the end of first end 52. Internal blunt tip 54 is blunted such that, under ordinary hand pressure, will not easily puncture human skin or other biological tissue. Internal cannula 50 further includes a second end 56, with a non-patient puncture tip 58 at the end of second end 56. Non-patient puncture tip 58 is provided for puncturing of an evacuated tube, for example, during a blood collection procedure. A central bore or internal lumen 60 extends through internal cannula 50 from internal blunt tip 54 to non-patient puncture tip 58, providing for the passage of fluid therethrough.

Figure 2:
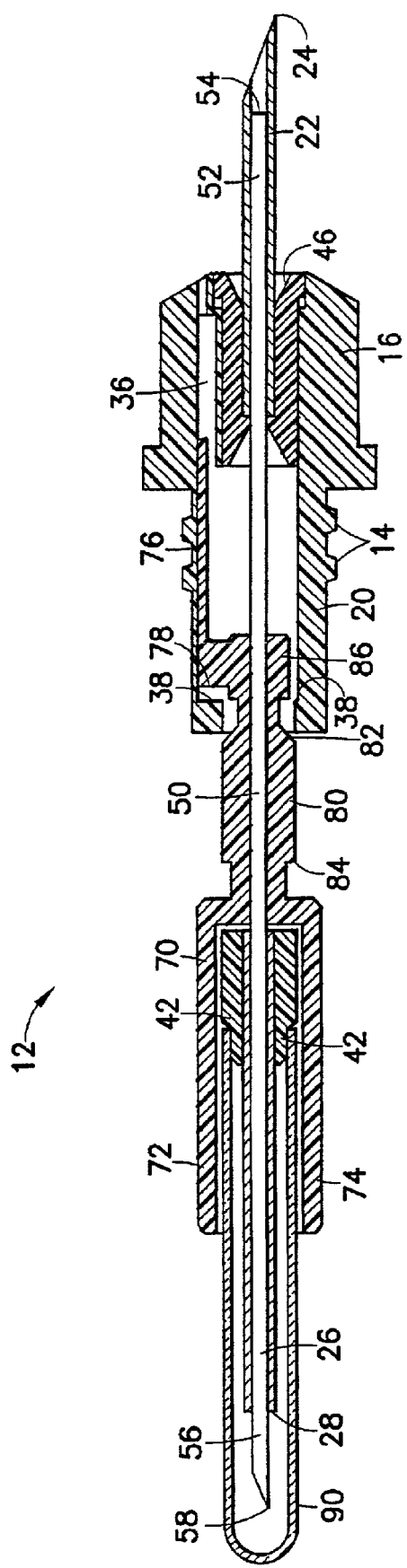
FIG. 2 is a cross sectional view of the dual blunting needle assembly of FIG. 1.
Figure 3:
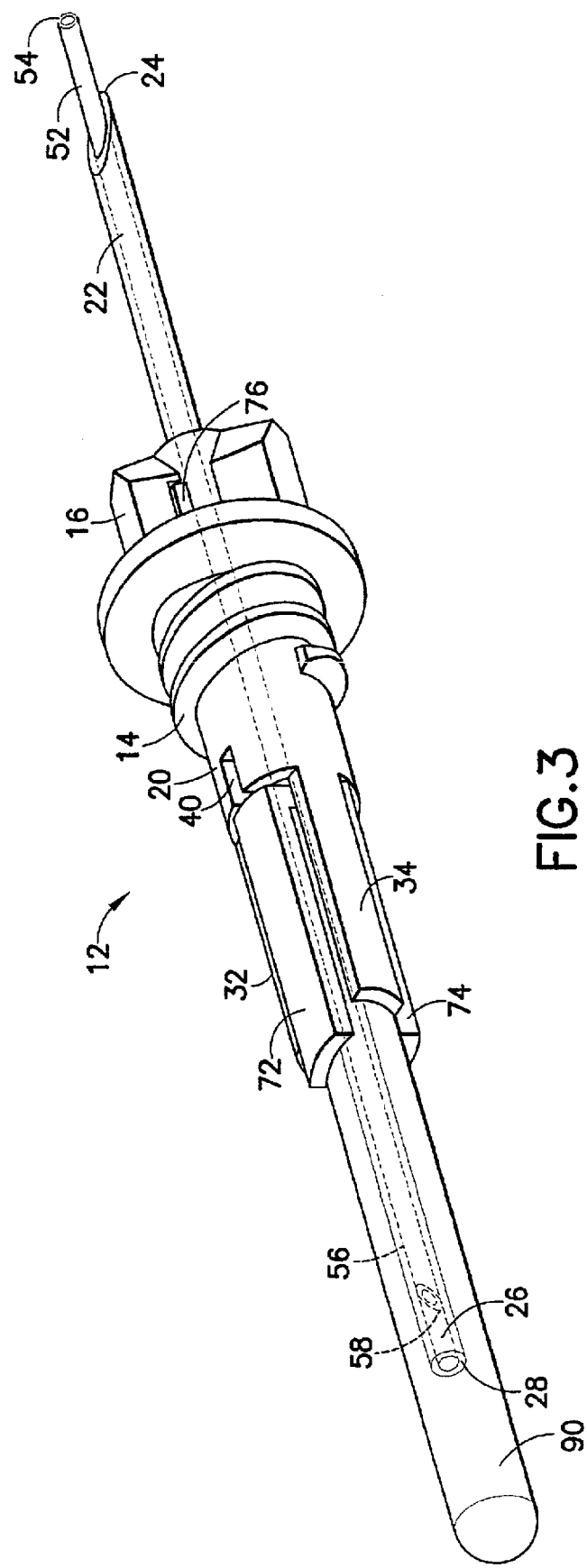
FIG. 3 is a perspective view of the dual blunting needle assembly of FIG. 1 shown in an activated position.
Figure 4:
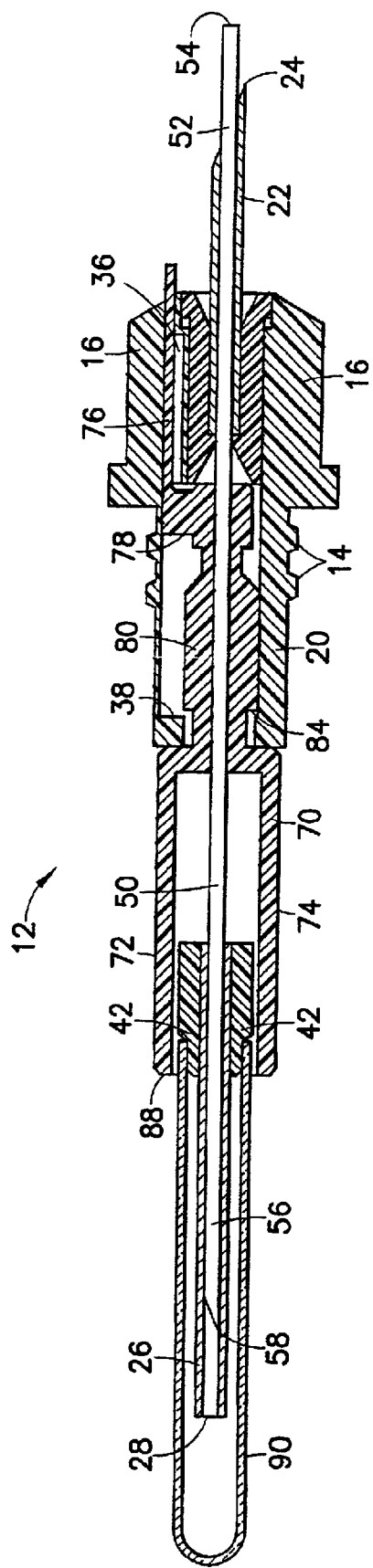
FIG. 4 is a cross sectional view of the activated needle assembly of FIG. 3.

As best depicted in FIG. 2, first end 52 of internal cannula 50 is adjacent first external cannula 22 of hub assembly 20, and second end 56 of internal cannula 50 is adjacent second external cannula 26 of hub assembly 20. Internal cannula 50 is axially slidable within the internal lumen 30 of hub assembly 20, such that internal blunt tip 54 is slidable within first external cannula 22 and non-patient puncture tip 58 is slidable within second external cannula 26. The inner diameter of first external cannula 22 is substantially the same as the outer diameter of first end 52 of internal cannula 50, and the inner diameter of second external cannula 26 is substantially the same as the outer diameter of second end 56 of internal cannula 50. As such, internal cannula 50 and hub assembly 20 are dimensioned and configured for a close fit, such that the external diameter of internal cannula 50 is a close fit with the internal diameter of hub assembly 20 so that intravenous puncture tip 24 lies flat on the external surface of first end 52 of internal cannula 50 and non-patient puncture tip 58 lies flat against the internal surface of second external cannula 26 within internal lumen 30 when needle assembly 12 is in an activated position, as shown in FIGS. 3 and 4 and described in more detail herein.

It may be desirable to lubricate the mating surfaces of internal cannula 50 and first and second external cannulas 22 and 26 of hub assembly 20, as well as to provide a seal between them to prevent the unwanted flow of air bubbles. Accordingly, a drop of viscous sealant-lubricant, such as petroleum jelly, may be provided about the mating surfaces thereof.

Internal cannula 50 is adapted for axial movement within internal lumen 30 of hub assembly 20 between a first retracted position in which intravenous puncture tip 24 and non-patient puncture tip 58 extend beyond internal blunt tip 54 and external blunt tip 28, respectively, and a second activated position in which internal blunt tip 54 and external blunt tip 28 extend beyond intravenous puncture tip 24 and non-patient puncture tip 58, respectively. More particularly, axial movement of internal cannula 50 within internal lumen 30 of hub assembly 20 in a direction of arrows 100 causes first end 52 of internal cannula 50 to axially displace with respect to first external cannula 22, which causes internal blunt tip 54 to extend beyond intravenous puncture tip 24 of first external cannula 22. In addition, such axial movement causes second end 58 of internal cannula 50 to axially displace with respect to second external cannula 26, which causes non-patient puncture tip 58 to slide within second external cannula 26 such that external blunt tip 28 extends beyond non-patient puncture tip 58, as depicted in FIGS. 3 and 4. As such, both intravenous puncture tip 24 and non-patient puncture tip 58 are simultaneously blunted.

Slidable engagement of internal cannula 50 and hub assembly 20 may be effected through carriage 70. Carriage 70 is concentric with internal cannula 50, and is provided for slidable engagement with hub assembly 20. Carriage 70 may be integral with internal cannula 50, or may be a separate member which is fixedly adhered to internal cannula 50 such as through the use of an adhesive. Carriage 70 is defined by a generally tubular body which includes arms 72 and 74 extending axially therealong and which are joined at nub 80. Arms 72 and 74 slidably engage arms 32 and 34 of hub assembly 20, such that the circumferential profile of needle assembly 12 about arms 72 and 74 of carriage 70 and arms 32 and 34 of hub assembly 20 is generally cylindrical or tubular, although other shapes or configurations may be apparent to those skilled in the art. In an alternative embodiment, carriage 70 may have arm 72 and may not have arm 74. In a further embodiment, carriage 70 may consist of multiple components. These embodiments may aid assembly of the device.

Nub 80 of carriage 70 includes a forward portion 86 which is positioned within the interior portion of hub assembly 20 when assembled. Forward portion 86 of carriage 70 includes a surface 78 which extends circumferentially about nub 80 for interference engagement with shoulder 38 of hub assembly 20. Such interference engagement prevents carriage 70, and therefore internal cannula 50 which is attached thereto, from being removed or disassembled from hub assembly 20 after assembly thereof. Nub 80 also includes a tapered surface 82 extending circumferentially therabout. Tapered surface 82 provides an interference engagement with hub assembly 20, preventing axial displacement of carriage 70 with respect to hub assembly 20 without a force exerted thereon, as will be described in more detail herein.

Nub 80 further includes rear face 88 which is adapted for engagement with the top surface of a blood collection tube during use. As will be discussed with respect to the use and operation of needle assembly 12, rear face 88 provides a mechanism for activating needle assembly 12, thereby axially displacing internal cannula 50 with respect to hub assembly 20 between a first retracted position and a second activated position.

Internal cannula 50 and hub assembly 20 may be reversibly axially displaceable with respect to each other, such that internal cannula 50 may displace with respect to hub assembly 20 from either the first retracted position to the second activated position or from the second activated position to the first retracted position. In preferred embodiments, internal cannula 50 is axially displaceable with respect to hub assembly 20 in only a single direction from the first retracted position to the second activated position. As such, needle assembly 12 may be provided with means for preventing axial displacement of internal cannula 50 from the second activated position to the first retracted position once it has been activated, such as a locking mechanism. For example, nub 80 may further include a surface 84 which extends circumferentially about nub 80 for interference engagement with shoulder 38 of hub assembly 20 after activation of needle assembly 12 from the first retracted position to the second activated position. Such interference engagement prevents axial movement of carriage 70 with respect to hub assembly 20 in a direction opposite arrows 100 after movement from the first retracted position to the second activated position.

Needle assembly 12 may be further provided with means for indicating movement of internal cannula 50 within hub assembly 20 between the first retracted position and the second extended position. Such means may be a visible, audible and/or tactile indicator, identifying movement of internal cannula 50 within hub assembly 20 between the first retracted position and the second extended position. For example, in one particular embodiment, hub assembly 20 may be provided with a channel 36 extending through the body thereof. Channel 36 is provided within hub assembly 20 and extends through the wall thereof to the external portion of needle assembly 12. Carriage 70 includes finger 76 which extends from forward portion 86 of nub 80 within channel 36 of hub assembly 20. Axial movement of carriage 70 with respect to hub assembly 20 causes finger 76 to axially slide within channel 36 of hub assembly 20. Upon axial movement of carriage 70 from the first retracted position shown in FIGS. 1–2 to the second activated position shown in FIGS. 3–4, finger 76 extends within channel 36 and through the wall of hub assembly 20, thereby providing an indication that needle assembly 12 has been activated, or blunted.

Channel 36 preferably extends through hub assembly 20 at a position which is beyond the point of attachment to a needle holder, such as threads 14, to ensure that such an indicator is visible to the user during operation and use. Moreover, finger 76 may be provided with a visual identification, such as a color code or verbiage to indicate activation of needle assembly 12.

Hub assembly 20 may further be provided with a means for attachment of a needle cover, such as shoulder 16 at the first end thereof. Shoulder 16 is provided for engagement with a needle cover (not shown), which covers intravenous puncture tip 24 of first external cannula 22 prior to use of the needle assembly 12 with a patient. Such a needle cover may be constructed of rigid polymeric material, as is known in the art. Shoulder 16 preferably includes a profile to provide for a frictional engagement with the needle cover, such that the needle cover is maintained in position about shoulder 16 in a friction fit, thereby covering and protecting first external cannula 22 and intravenous puncture tip 24 until assembly and use.

Also, needle assembly 12 may be provided with a second needle cover (not shown) for covering non-patient puncture tip 58 of second external cannula 26 prior to assembling of needle assembly 12 with a needle holder. Such a second needle cover may also be constructed of rigid polymeric material. This second needle cover may be attached to needle holder 12, for example, by threaded engagement with external threads 14 extending about hub assembly 20. In this manner, this second needle cover can be removed from needle assembly 12 prior to assembly with a needle holder by unthreading the needle cover from external threads 14, and then threading external threads 14 into an internal thread of such a needle holder, as is known in the art.

Needle assembly 12 is further provided with an elastomeric sleeve 90 extending about second external cannula 26 and second end 56 of internal cannula 50, and covering non-patient puncture tip 58, as is generally known in the art. Elastomeric sleeve 90 is joined to bridge member 42. This joining means may be an interference mechanism, a snap-fit, an adhesive, or other such similar means.

Figure 5:
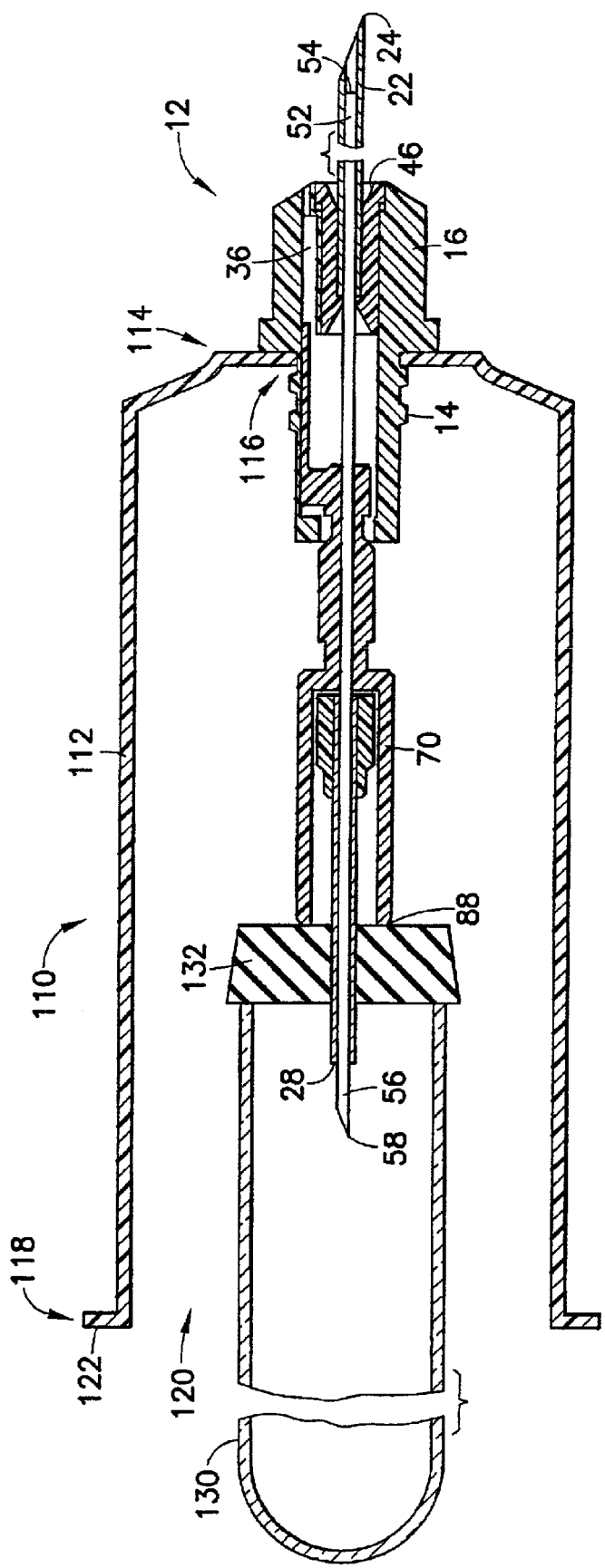
FIG. 5 is a cross-sectional view of the needle assembly of the present invention shown in a retracted position in use with a needle holder and an evacuated collection tube.
Figure 6:
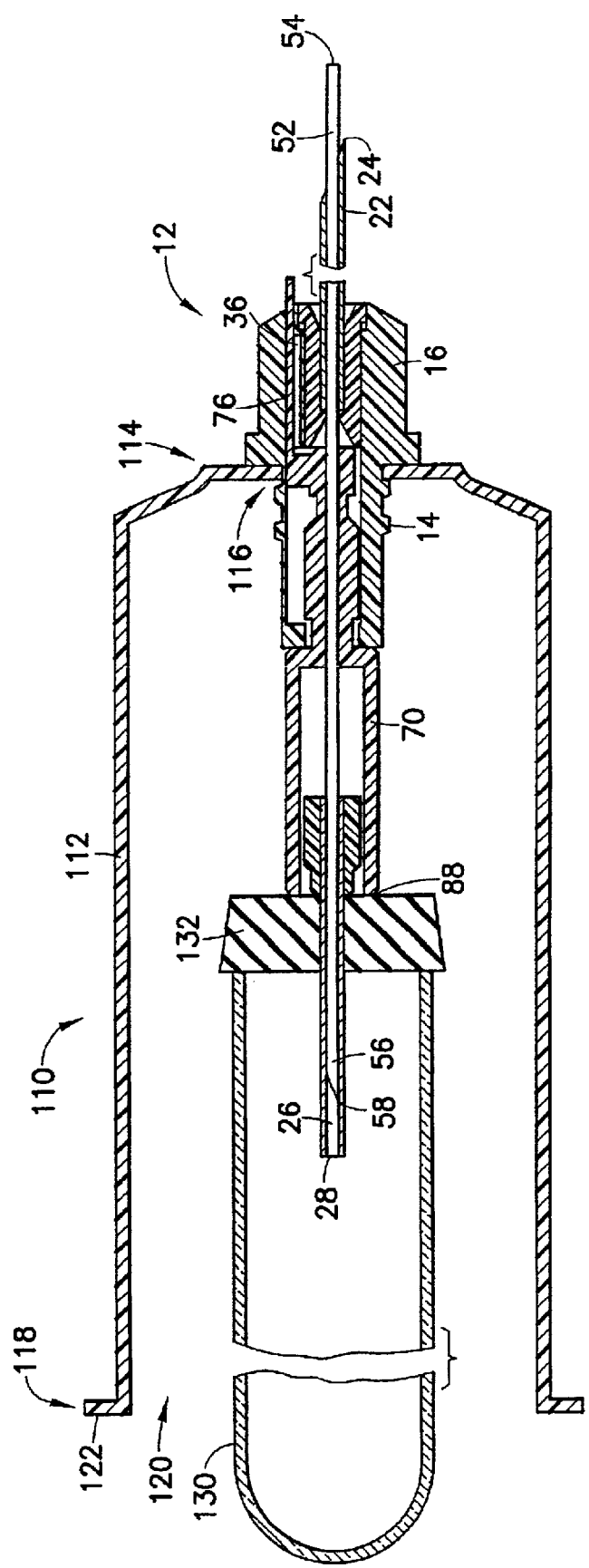
FIG. 6 is a cross-sectional view of the needle assembly of the present invention shown in an activated position in use with a needle holder and an evacuated collection tube.

In a further embodiment, the present invention is directed to a safety assembly which includes needle assembly 12 in combination with a needle holder 110, as shown in FIGS. 5 and 6. Needle holder 110 may be a conventional needle holder as is well known in the art for use in connection with double-ended needles for blood collection. For example, needle holder 110 is defined generally by hollow body 112, which includes first end 114, and second end 118. First end 114 of needle holder 110 includes an opening 116 extending therethrough, while second end 118 includes flange 122 and is generally open-ended, providing needle holder 110 with a hollow body 112 having an internal opening 120 extending therethrough. Such internal opening 120 accommodates a blood collection tube 130 during a sampling procedure, such as an evacuated collection tube, as is known in the art.

Means for attachment are provided for attaching needle assembly 12 to needle holder 110, such as within internal opening 116 at first end 114. Such attachment may be accomplished, for example, through a snap-fit engagement, or more desirably, through a threaded relation, such as through internal threads within opening 116 for engagement with external threads 14 of needle assembly 12.

Operation and use of the needle assembly of the present invention will now be described in terms of the embodiment depicted in FIGS. 1–4. In use, needle assembly 12 is provided including a first needle cover (not shown) extending over first external cannula 22, and a second needle cover (not shown) extending over second external cannula 26. When preparing the needle assembly for use in a sampling procedure, the second needle cover is removed from second external cannula 26, and needle assembly 12 is then attached to needle holder 110, such as by threading external threads 14 with internal threads provided within opening 116 of needle holder 110.

The needle cover extending over first external cannula 22 is then removed. Venipuncture is then conducted in known manner, whereby intravenous puncture tip 24 is inserted into a vein of a patient, and evacuated blood collection tube 130 having pierceable closure 132 is inserted into the needle holder, such that pierceable closure 132 of the collection tube 130 contacts sleeve 90 extending about second external cannula 26. When slight pressure is exerted on the collection tube 130, pierceable closure 132 contacting sleeve 90 causes sleeve 90 to displace, thereby causing non-patient puncture tip 58 to puncture sleeve 90 and, in turn, pierceable closure 132. At such time, the interior of collection tube 130 and internal lumen 60 of internal cannula 50 are in fluid communication. Since the interior of collection tube is at a negative pressure, blood is drawn from the vein of the patient, through internal lumen 30 of first external cannula 22, through internal lumen 60 of internal cannula 50 and into collection tube 130.

When all desired samples have been drawn, activation of the dual blunting needle assembly is accomplished. Activation of the dual blunting needle assembly is desirably accomplished while venipuncture is maintained, that is while intravenous puncture tip 24 of first external cannula 22 is maintained within the vein of the patient, in order to prevent an accidental needle stick prior to blunting of the needle. Blunting of the needle assembly 12 is accomplished exerting pressure in a direction of arrows 100 on rear face 88 of carriage 70.

In particular, during sampling, the top surface of pierceable closure 132 of collection tube 130 contacts rear face 88 of carriage 70 within the holder. When additional force is exerted against collection tube 130 in a direction of arrows 100, rear face 88 is forced in the direction of arrows 100. Such force causes interference engagement between tapered surface 82 of nub 80 against hub assembly 20. Since hub assembly 20 includes groove 40 at opposed portions of the wall thereof, hub assembly 20 radially displaces to permit tapered surface 82 to pass within hub assembly 20, thereby causing axial movement of carriage 70 with respect to hub assembly 20. Moreover, since arms 72 and 74 of carriage 70 interfit with arms 32 and 34 of hub assembly 20, carriage 70 is able to axially slide with respect to hub assembly 20.

Since carriage 70 is attached to internal cannula 50, axial displacement of carriage 70 with respect to hub assembly 20 causes axial displacement of internal cannula 50 with respect to hub assembly 20. Moreover, since first external cannula 22 and second external cannula 26 are attached to hub assembly 20, axial displacement of internal cannula 50 with respect to hub assembly 20 causes first end 52 and second end 56 to axially displace with respect to first external cannula 22 and second external cannula 26. Since internal blunt tip 54 and external blunt tip 28 are positioned short of intravenous puncture tip 24 and non-patient puncture tip 58, respectively, axial displacement of first end 52 and second end 56 with respect to first external cannula 22 and second external cannula 26 causes internal blunt tip 54 and external blunt tip 28 to axially displace to a position in which they extend beyond intravenous puncture tip 24 and non-patient puncture tip 58, respectively. More particularly, when internal cannula 50 is axially displaced in the direction of arrows 100, internal blunt tip 54 protrudes from the end of first external cannula 22 beyond intravenous puncture tip 24, and non-patient puncture tip 58 slides within second external cannula 26 such that external blunt tip 28 extends beyond non-patient puncture tip 58, as depicted in FIGS. 3 and 4. As such, both intravenous puncture tip 24 and non-patient puncture tip 58 are simultaneously blunted. Needle assembly 10 can then be removed from the patient's vein, and appropriately discarded.

As noted, the safety assembly of the present invention includes needle assembly 12 used in connection with a needle holder 110, which may be a standard needle holder known for use with conventional double-ended needle assemblies for blood collection. Desirably, the safety assembly includes a needle holder which is particularly designed for use in connection with a needle assembly having an activation mechanism such as a blunting member adapted for axial displacement between a first retracted position and a second activated or blunted position, such as needle assembly 12 of the present invention. In particularly preferred embodiments, needle holder 110 includes a mechanism for causing axial displacement of internal cannula 50 within internal lumen 30 of hub assembly 20.

Figure 7:
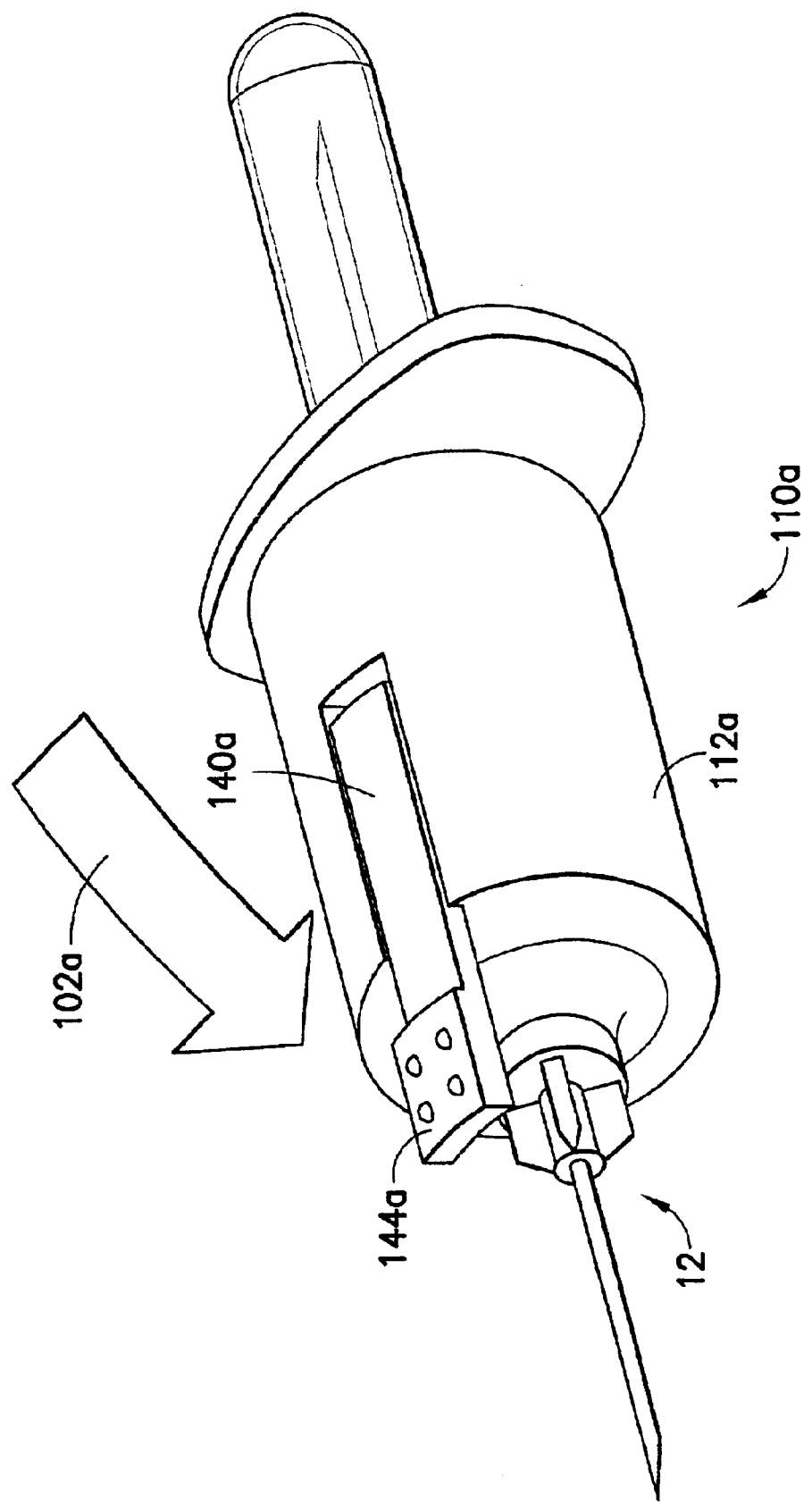
FIG. 7 is a perspective view of the needle assembly of the present invention shown in use with an alternate needle holder.
Figure 8:
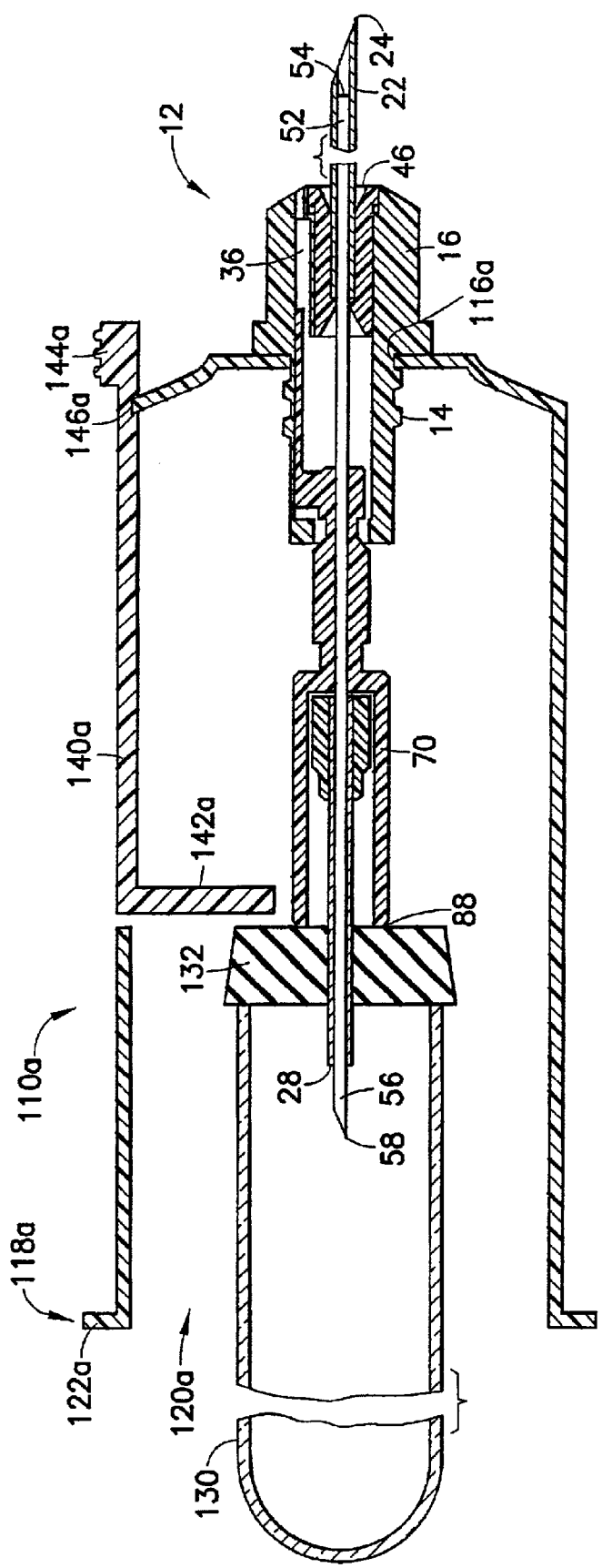
FIG. 8 is a cross-sectional view of the needle assembly of the present invention shown in a retracted position in use with the needle holder of FIG. 7.
Figure 9:
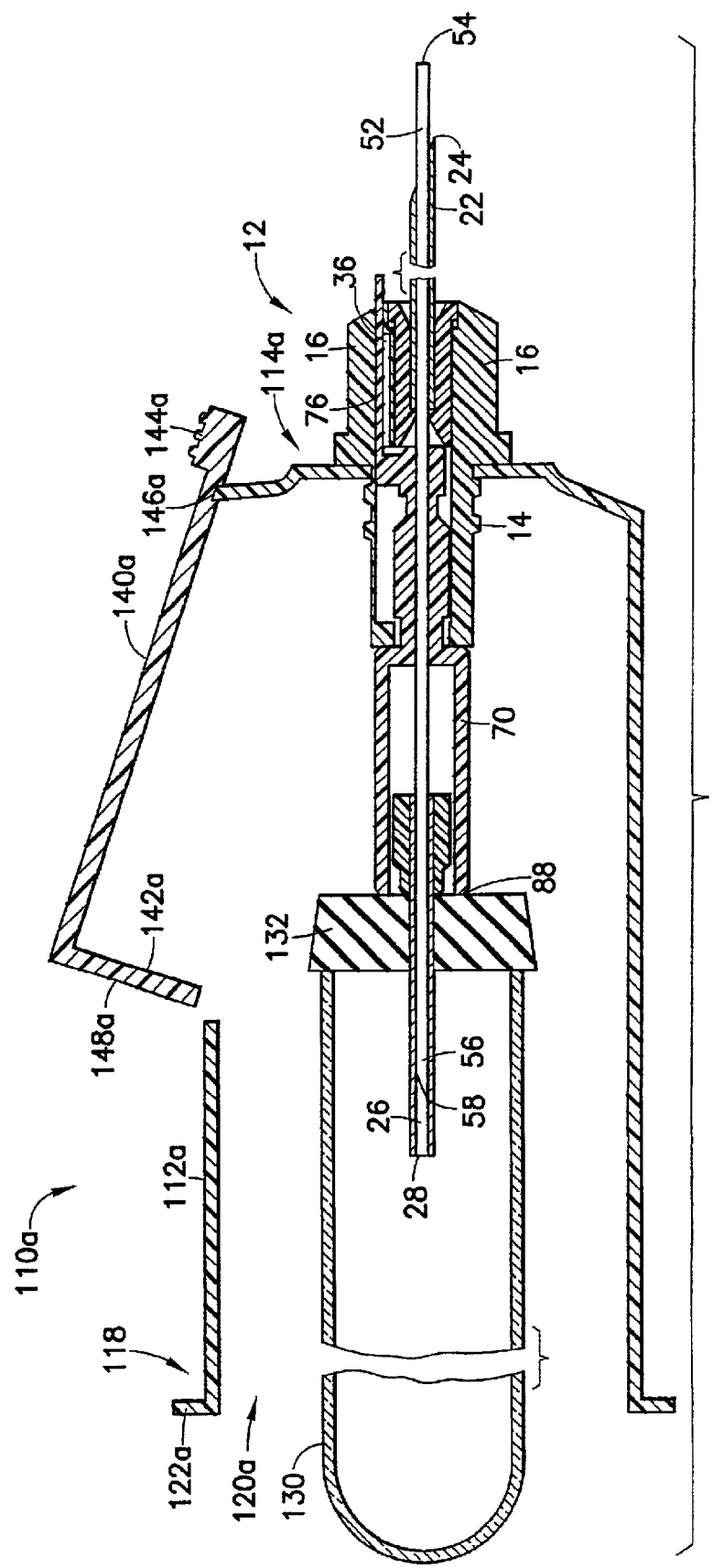
FIG. 9 is a cross-sectional view of the needle assembly of the present invention shown in an activated position in use with the needle holder of FIG. 7.

For example, as depicted in FIGS. 7–11, the safety assembly may include a needle holder which includes a lever for preventing or permitting activation of needle assembly 12. In particular, as shown in FIGS. 7–9, needle holder 110a is provided. Needle holder 110a includes a generally tubular hollow body 112a, including first end 114a and second end 118a. First end 114a of needle holder 110a includes an opening 116a extending therethrough, while second end 118a includes flange 122a and is generally open-ended, providing needle holder 110a with a hollow body 112a having an internal opening 120a extending therethrough. Such internal opening 120a accommodates a blood collection tube 130 during a sampling procedure, such as an evacuated collection tube, as is known in the art.

Means for attachment are provided for attaching needle assembly 12 to needle holder 110a, such as within internal opening 116a at first end 114a. Such attachment may be accomplished, for example, through a snap-fit engagement, or more desirably, through a threaded relation, such as through internal threads within opening 116a for engagement with external threads 14 of needle assembly 12.

Needle holder 110a is further provided with a lever 140a extending along a portion of hollow body 112a thereof. Lever 140a is provided as a generally elongated portion extending axially along the exterior portion of hollow body 112a. Lever 140a includes extension arm 142a extending from one end thereof. Extension arm 142a extends through the wall of hollow body 112a of needle holder 110a, and within internal opening 120a of needle holder 110a. Extension arm 142a includes surface 148a, which is provided for interfering engagement with a top surface of collection tube 130 such as pierceable closure 132.

Lever 140a is movable between a first blocking position and a second release position. More particularly, lever 140a is provided in a first position in which lever 140a lies flush with the outer surface of hollow body 112a of needle holder 110a, such that lever 140a represents a continuation of the outer surface of hollow body 112a of needle holder 110a. In such a first position, extension arm 142a extends within internal opening 120a for interfering or abutting engagement with pierceable closure 132 of a collection tube 130 inserted within internal opening 120a. In such a first position, collection tube 130 is blocked from engagement with carriage 70 to prevent axial displacement of carriage 70, and therefore prevent axial displacement of internal cannula 50 with respect to hub assembly 20 between the first retracted position and the second activated position.

Lever 140a is movable in a direction of arrow 102a to a second release position, in which lever 140a protrudes from the outer surface of hollow body 112a of needle holder 110a. In such a second position, extension arm 142a is moved out of interfering or abutting engagement with pierceable closure 132 of collection tube 130 within internal opening 120a. As such, collection tube 130 is permitted to engage with carriage 70. Application of force on collection tube 130 such as by pushing collection tube 130 further within internal opening 120a of needle holder 110a causes engagement of pierceable closure 132 against surface 88 of carriage 70. Such engagement results in axial displacement of carriage 70, and therefore axial displacement of internal cannula 50 with respect to hub assembly 20 between the first retracted position and the second activated position, as discussed above. As such, lever 140a provides a blocking mechanism for preventing axial displacement of internal cannula 50 with respect to hub assembly 20, and therefore for preventing blunting of needle assembly 12, until a desired time.

Movement of lever 140a between the first blocking position and the second release position may be provided through hinge 146a. Hinge 146a is depicted in FIGS. 7–9 at first end 114a of needle holder 110a. Lever 140a may be provided as a separate member which is attached to hollow body 112a of needle holder 110a at hinge 146a. More desirably, lever 140a is integrally formed with hollow body 112a of needle holder 110a. For instance, lever 140a may be provided as a cutaway portion of hollow body 112a, with lever 140a and hollow body 112a being interconnected through hinge 146a.

Lever 140a further includes tab 144a, which is provided for moving lever 140a between the first blocking position and the second release position. Tab 144a may be provided at a position adjacent first end 114a of needle holder 110a, with tab 144a extending from hollow body 112a, to a position adjacent the connection between needle holder 110a and needle assembly 12. In this manner, tab 144a can be activated by applying pressure in a direction of arrow 102a, such that tab 144a deflects, thereby activating and moving lever 140a between the first blocking position and the second release position, as shown in FIG. 9.

Figure 10:
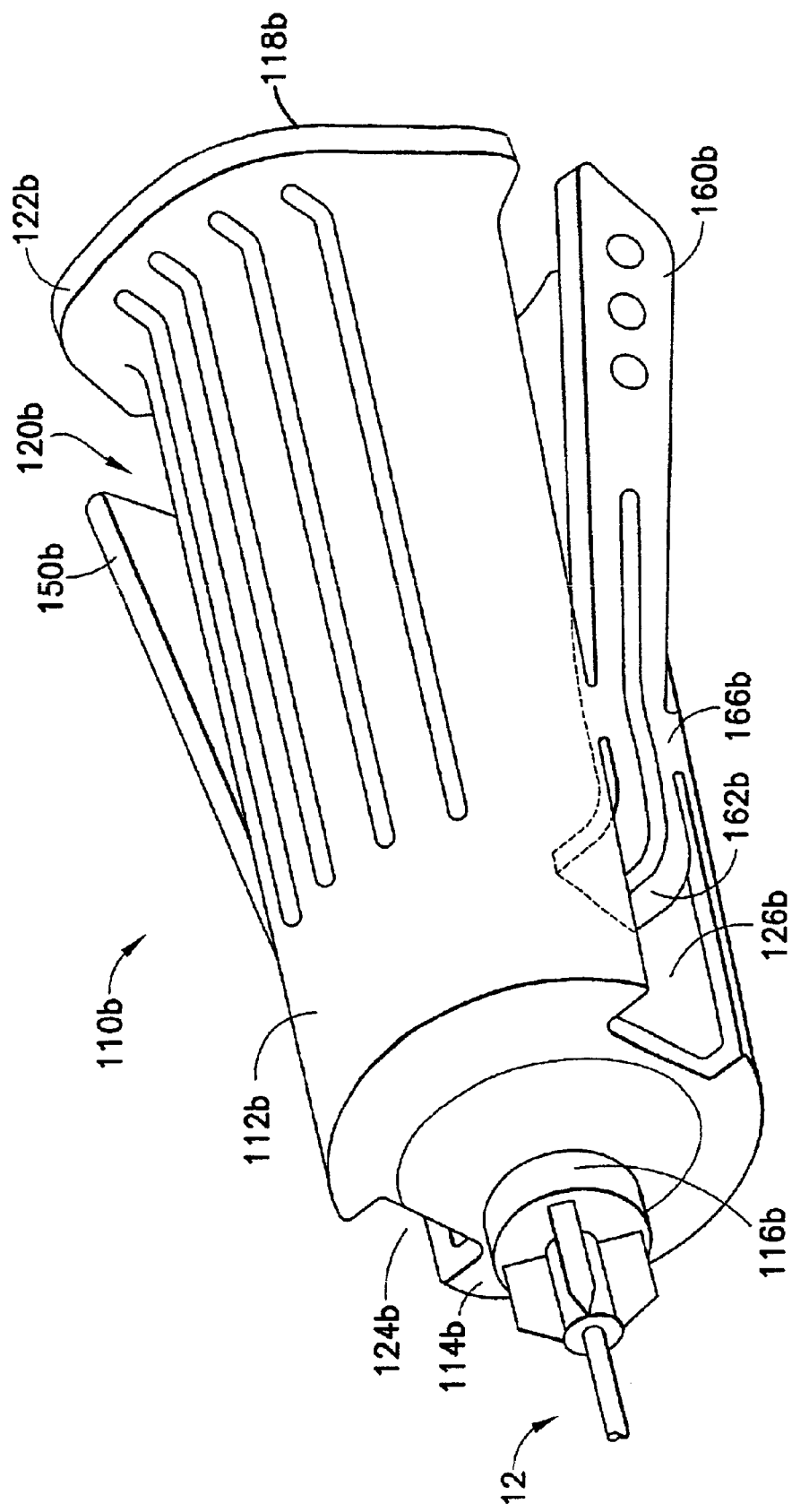
FIG. 10 is a perspective view of the needle assembly of the present invention shown in use with a further alternate needle holder.
Figure 11:
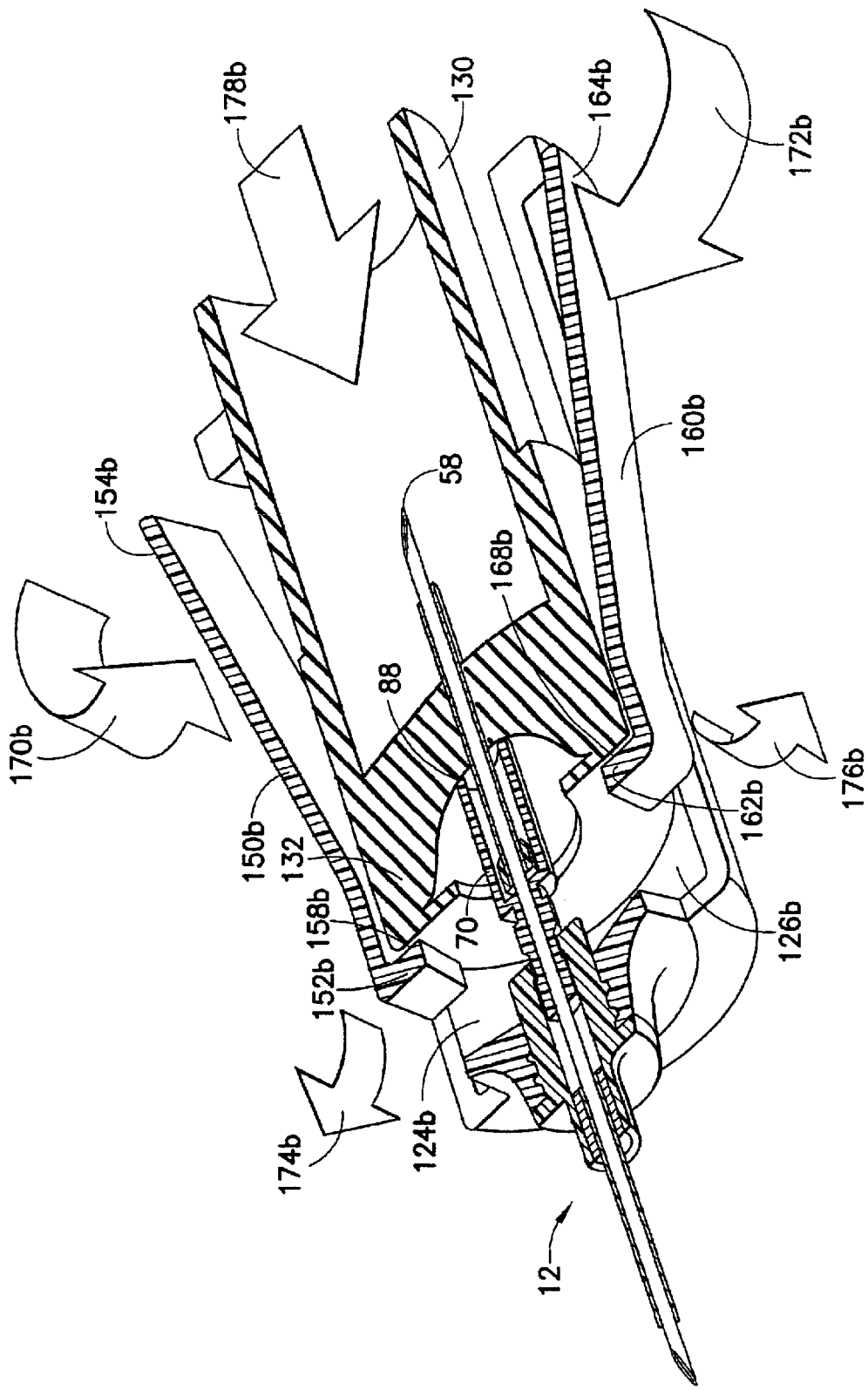
FIG. 11 is a perspective cross-sectional view of the needle assembly of the present invention shown in a retracted position in use with the needle holder of FIG. 10.

In a further embodiment shown in FIGS. 10 and 11, needle holder 110b includes hollow body 112b including first end 114b having opening 116b and second end 118b having flange 122b, and internal opening 120b extending therethrough. Needle holder 110b includes a pair of levers 150b and 160b in a similar manner as lever 140a shown in the embodiment of FIGS. 7–9. In particular, first lever 150b and second lever 160b include tabs 154b and 164b, extension arms 152b and 162b and surfaces 158b and 168b, respectively. First lever arm 150b and second lever arm 160b extend along opposing sides of hollow body 112b of needle holder 110b within channels 124b and 126b respectively. In such an embodiment, first lever 150b and second lever 160b may extend away from hollow body 112b in a flaring manner, with tabs 158b and 168b positioned adjacent second end 118b of needle holder 110b.

Movement of first lever 150b and second lever 160b between the first blocking position and the second release position can be accomplished through activation of tabs 154b and 164b by applying pressure in a direction of arrow 170b and 172b. As such, tab 154b and 164b deflect, thereby causing extension arms 152b and 162b to deflect outward in a direction of arrows 174b and 176b, respectively. Such deflection moves first and second levers 150b and 160b between the first blocking position and the second release position, thereby releasing collection tube 130 from the blocked position. As such, collection tube 130 can be forwarded in a direction of arrow 178b, thereby activating needle assembly 12 through engagement between pierceable closure 132 and carriage 70, as described above. In an alternative embodiment, needle holder 160b may have lever 150b and may not have lever 160b.

In a further embodiment, the needle holder may be provided with a mechanism for activating the blunting mechanism of the needle assembly, such as by axially displacing the internal cannula within the internal lumen between the first retracted position and the second activated position. For example, the needle holder may include a rotational mechanism including an internal cam assembly for blunting of an intravenous puncture tip of a needle assembly. Desirably, such a mechanism is adapted for engagement with the carriage for axially displacing the internal cannula.

Examples of particularly desirable embodiments of such needle holders are depicted in FIGS. 12–21. In the embodiment depicted in FIGS. 12–17, a needle holder 110c includes an outer body 180e for attachment to a needle assembly, such as needle assembly 12 as described hereinabove. Outer body 180c includes a first end 182c adapted for attachment to needle assembly 12, and an open-ended second end 184c, with an interior space 186c within outer body 180e extending from first end 182c to second end 184c. Needle holder 110c further includes a mechanism extending within interior space 186c of outer body 180c for engagement with carriage 70 of needle assembly 12, for causing said axial displacement of internal cannula 50 between the first retracted position and the second activated position. As shown in FIGS. 12–14, such a mechanism may be in the form of an inner body 190c which is concentric with and extends within interior space 186c of outer body 180c through second end 184c.

Inner body 190c is in slidable engagement within outer body 180c. Inner body 190c includes first end 192c which extends within interior space 186c of outer body 180c, and second end 194c which protrudes from second end 184c of outer body 180c. Inner body 190c further includes an interior space 196c, which is adapted for accommodating a blood collection tube therein for sampling procedures, as described hereinabove.

Activation of the blunting feature of needle assembly 12 can be accomplished in such an embodiment by sliding inner body 190c within outer body 180c in a direction of arrow 200. Such sliding forces first end 192c of inner body 190c to engage carriage 70 at rear face 88, thereby forcing carriage 70 to move in the direction of arrow 200, which activates the blunting feature of needle assembly 12, as described in detail above. Sliding of inner body 190c within outer body 180c can be easily accomplished by the user with slight pressure exerted on second end 194c of inner body 190c in the direction of arrow 200.

It is noted that inner body 190c may alternatively be in rotational engagement within outer body 180c, such as through interrelating and mating threads on an outer surface of inner body 190c and an inner surface of outer body 180c. As such, activation of the blunting feature can be achieved by rotating inner body 190c within outer body 180c such as by screwing the mating threads, thereby screwing inner body 190c within outer body 180c in a direction of arrow 200.

As shown clearly in FIGS. 12–14, outer body 180c may further be provided with an opening 188c extending through the wall thereof. In addition, inner body 190c may be provided with a protrusion such as finger 198c, which is adapted for engagement within opening 188c of outer body 180c when inner body 190c is slidably moved in the direction of arrow 200. Such engagement between finger 198c and opening 188c provides holder 100c with a locking feature, wherein inner body 190c is prevented from slidably moving within outer body 180c in a reverse direction once moved in the direction of arrow 200. As such, inner body 190c is locked in place within outer body 180c, which in turn locks carriage 70 of needle assembly 12 in place, thereby effectively locking needle assembly 12 in the second extended position for blunting.

Figure 15:
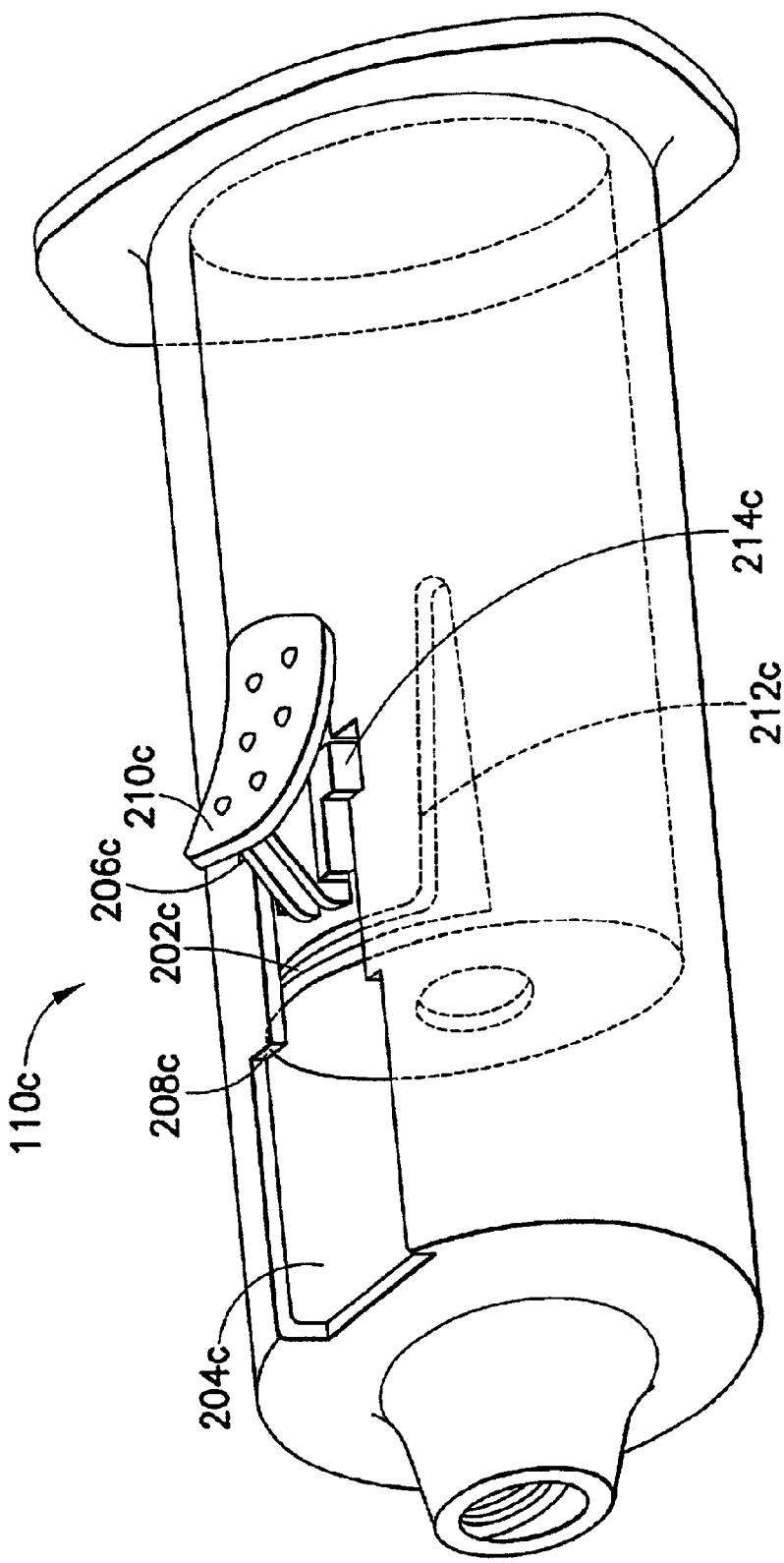
FIG. 15 is a perspective view of the needle assembly of the present invention shown in use with yet a further alternate needle holder.
Figure 16:
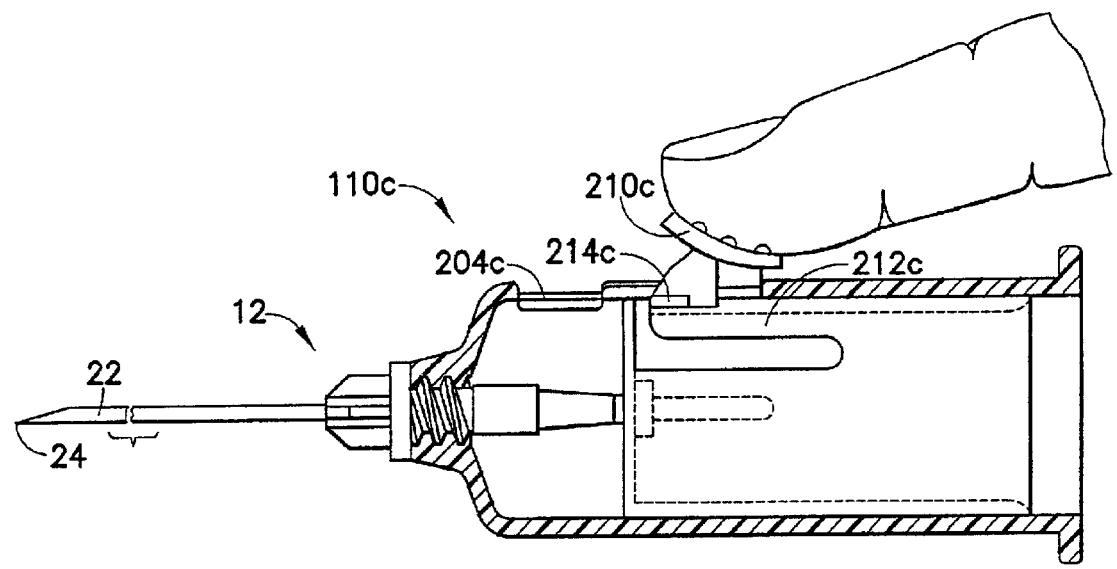
FIG. 16 is a cross-sectional view of the needle assembly of the present invention shown in a retracted position in use with the needle holder of FIG. 15.
Figure 17:
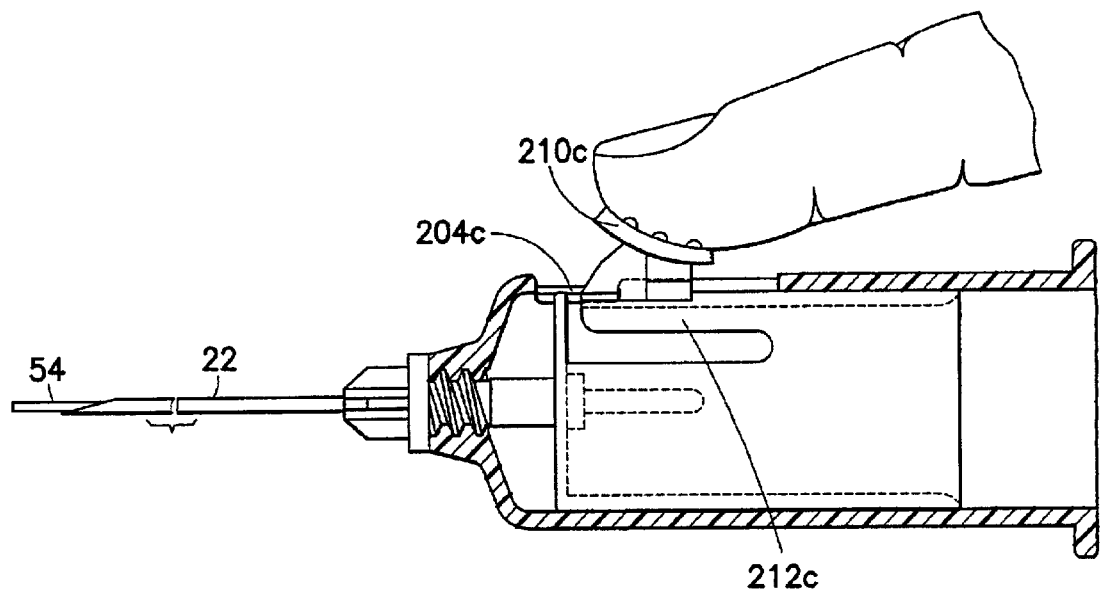
FIG. 17 is a cross-sectional view of the needle assembly of the present invention shown in an activated position in use with the needle holder of FIG. 15.
Figure 18:
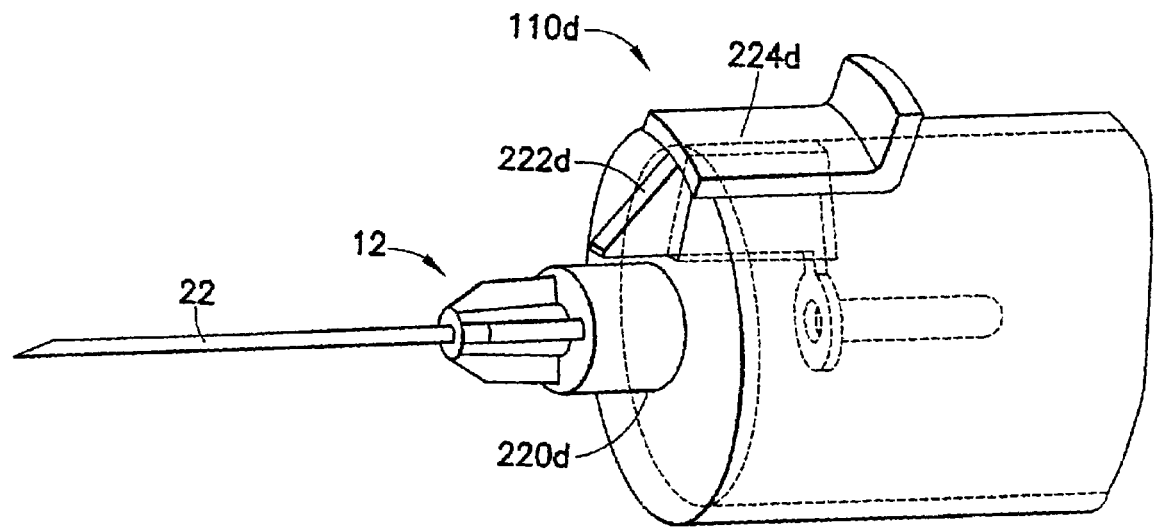
FIG. 18 is a perspective view of the needle assembly of the present invention shown in use with a further alternate needle holder.
Figure 19:
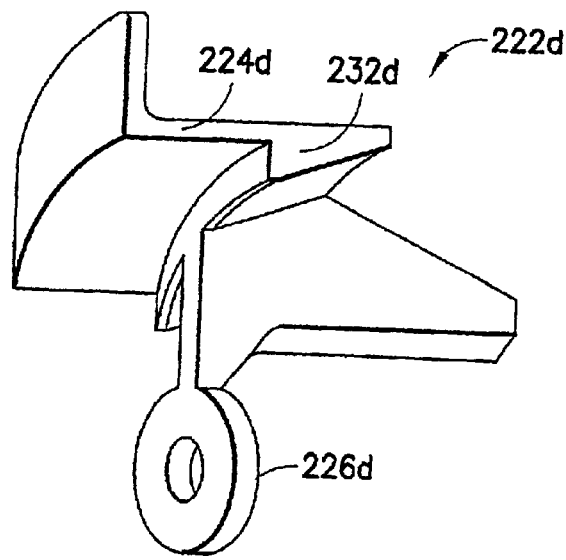
FIG. 19 is a perspective view of the tab mechanism of the needle holder of FIG. 18.
Figure 20:
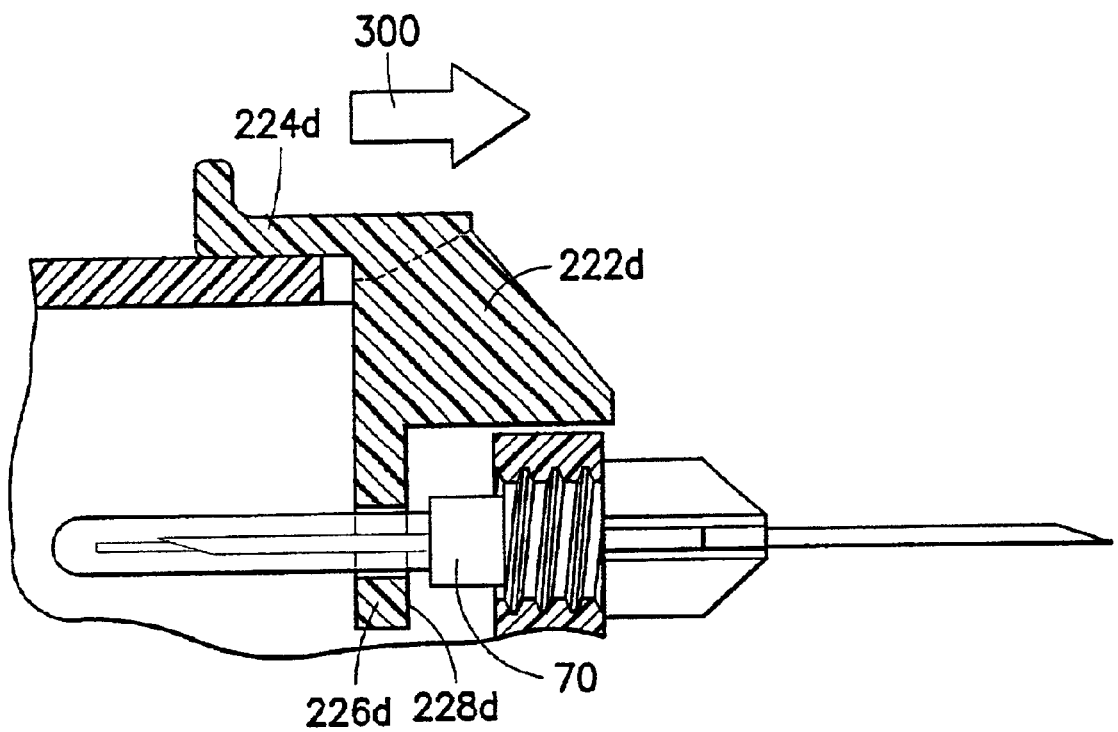
FIG. 20 is a cross-sectional view of the needle assembly of the present invention shown in a retracted position in use with the needle holder of FIG. 18.

Moreover, activation of the blunting feature of needle assembly 12 can be accomplished by sliding inner body 190c within outer body 180c by way of cooperating features of inner body 190c and outer body 180c. For example, outer body 180c may include a channel 202c extending axially along an outer surface thereof, as depicted in FIGS. 15–17. Channel 202c desirably includes an expanded opening 204c at first end 182c of outer body 180c. First lip 206c extends at a first position within channel 202c, while second lip 208c extends at the juncture of channel 202c and opening 204c. Inner body 190c includes tab 210c extending from an outer surface thereof. For example, inner body 190c may include a cutaway portion 212c, which flexes upon application of force. Tab 210c is integrally formed with cutaway portion 212c, with shoulder 214c extending therebetween.

Channel 202c accommodates tab 210c in slidable engagement therein. In a first position such as during sampling, shoulder 214c is in interference engagement with first lip 206c. When activation of the blunting feature of needle assembly 12 is desired, tab 210c is depressed, which flexes cutaway portion 212c within interior space 196c of inner body 190c, thereby releasing shoulder 214c from interference engagement with first lip 206c. Forward slidable movement of inner body 190c within outer body 180c can then be accomplished through movement of tab 210c. Once tab 210c is moved to a position adjacent opening 204c, tab 210c flexes upward such that tab 210c extends outward through opening 204c. Shoulder 214c is then in interference engagement with second lip 208c, thereby providing a locking feature, wherein inner body 190e is prevented from slidably moving within outer body 180c in a reverse direction.

Yet a further needle holder embodiment is depicted in FIGS. 18–21. Such a needle holder 110d includes a tubular hollow body in a similar manner as tubular hollow body 112 which is described above with respect to FIGS. 5 and 6, with a slot 220d extending therethrough. Needle holder 110d further includes a mechanism 222d which extends through slot 220d. Mechanism 222d is adapted for engagement with carriage 70 of a needle assembly, for axially displacing the internal cannula of the needle assembly as described above.

Mechanism 222d includes a tab 224d adapted for finger activation by a user. Mechanism 222d further includes extension 226d which extends from tab 224d through slot 220d. Extension 226d includes surface 228d for engagement with carriage 70 of a needle assembly. Activation of the blunting feature of needle assembly 12 can be accomplished in such an embodiment by sliding mechanism 222d in a direction of arrow 300. Such sliding forces surface 228d of mechanism 222d to engage carriage 70 at rear face 88, thereby forcing carriage 70 to move in the direction of arrow 300, which activates the blunting feature of needle assembly 12, as described in detail above. Sliding of mechanism 222d can be easily accomplished by the user with slight pressure exerted on tab 224d in the direction of arrow 300.

Figure 21:
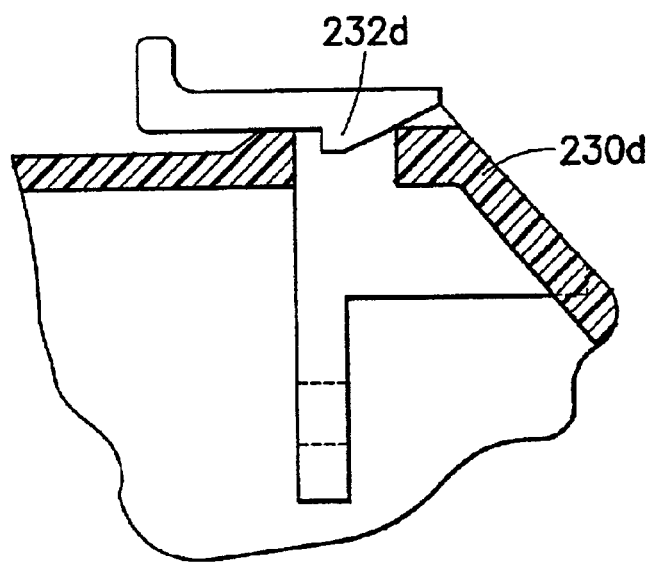
FIG. 21 is a cross-sectional view of the needle assembly of the present invention shown in an activated position in use with the needle holder of FIG. 18.

As shown clearly in FIG. 21, holder 110d may be provided with a locking feature, wherein mechanism 222d is prevented from slidably moving in a reverse direction once moved in the direction of arrow 300. This may be accomplished by providing opening 230d, and providing mechanism 222d with a finger 232d on an underside thereof. Such finger 232d is provided for interference engagement with the edge of opening 230d, thereby providing a locking feature, wherein mechanism 222d is prevented from slidably moving in a reverse direction.

It is noted that the needle holders described above, particularly in connection with FIGS. 11–21, can be used with any needle assembly which includes an activation mechanism such as a blunting member adapted for axial displacement between a first retracted position and a second activated or blunted position. Accordingly, such needle holders can be used with needle assemblies which include a double blunting needle, such as needle assembly 12 described above, as well as needle assemblies which include only a single blunting needle.

The needle assembly of the present invention may be comprised of moldable parts which can be mass produced from a variety of materials including, for example, polyethylene, polyvinyl chloride, polystyrene or the like. Materials can be selected which will provide the proper support for the structure of the invention in its use, and which will also provide a degree of resiliency for the purpose or providing the cooperative relative movement.

While the needle assembly of the present invention has been described in terms of one embodiment for use in connection with a blood collection system, it is further contemplated that the needle assembly could be used with other medical procedures, such as in conjunction with a conventional intravenous infusion set, as which are well known in the art for use with conventional needle assemblies.

What is claimed:

1. A needle holder in combination with a needle assembly which includes an activation mechanism configured for axial displacement between a first retracted position and a second activated position with respect to said needle assembly, said needle holder comprising:

an outer body having a first end adapted for attachment to said needle assembly and a second end having an internal opening therein; and an inner body slidable within said outer body and having a tubular body concentric with said outer body, said tubular body of said inner body including a first end and an opposed second end, said first end of said inner body including a mechanism adapted for engagement with said activation mechanism of said needle assembly for axially displacing said activation mechanism between said first retracted position and said second activated position, said second end of said tubular body of said inner body projecting outwardly beyond said second end of said outer body and including an internal opening for accommodating a blood collection tube therein, the inner body and the outer body having locking elements that engage to prevent sliding movement of the inner body relevant to the outer body after the activation mechanism is in the second activated position.

2. A needle holder in combination with a needle assembly as in claim 1, wherein said first end of said tubular body of said inner body includes an opening for accommodating a puncture tip of said needle assembly.

3. A needle holder in combination with a needle assembly as in claim 1, wherein said outer body includes means for attachment to said needle assembly.

4. A needle holder in combination with a needle assembly as in claim 3, wherein said means for attachment comprises internal threads.

5. A blood collection assembly comprising:
   a) a needle assembly including an activation mechanism which is adapted for axial displacement between a first retracted position and a second activated position with respect to said needle assembly, said activation mechanism adapted for axial displacement; and
   b) a needle holder attached to said needle assembly, said needle holder including an outer body having a first end adapted for attachment to said needle assembly and a second end having an internal opening therein, said needle holder further including an inner body slidable within said outer body, said inner body including opposite first and second ends, said first end of said inner body being disposed within said outer body and being configured for engaging and axially displacing said activation mechanism between said first retracted position and said second activated position, said second end of said inner body projecting outwardly from said outer body and having an internal opening for accommodating a blood collection tube therein, the inner body and the outer body having locking elements that engage to prevent sliding movement of the inner body relevant to the outer body after the activation mechanism is in the second activated position.

6. A safety collection assembly comprising:
   a) a safety needle assembly including an intravenous puncture tip, a non-patient puncture tip, and a blunting member having a blunted tip, said blunting member adapted for axial displacement with respect to said intravenous puncture tip between a first retracted position in which said intravenous puncture tip extends beyond said blunted tip and a second activated position in which said blunted tip extends beyond said intravenous puncture tip; and
   b) a needle holder attached to said needle assembly, said needle holder including an outer body having a first end adapted for attachment to said needle assembly and a second end having an internal opening therein, said needle holder further including an inner body slidable within said outer body, said inner body having opposite first and second ends, said first end of said inner body being disposed within said outer body and being configured for engagement with said blunting member for axial displacement of said blunting member with respect to said intravenous puncture tip, said second end of said inner body projecting outwardly from said outer body and having an internal opening for accommodating a blood collection tube therein, the inner body and the outer body having locking elements that engage to prevent sliding movement of the inner body relevant to the outer body after the activation mechanism is in the second activated position.

7. A safety collection assembly as in claim 6, wherein said needle assembly includes an activation mechanism for causing said axial displacement of said blunting member with respect to said intravenous puncture tip, and said inner body is adapted for engagement with said activation mechanism.

8. A safety collection assembly comprising:
   a) a safety needle assembly including an intravenous puncture tip, a non-patient puncture tip, a first blunting member having a blunted tip, said first blunting member adapted for axial displacement with respect to said intravenous puncture tip between a first retracted position in which said intravenous puncture tip extends beyond said first blunted tip and a second activated position in which said blunted tip extends beyond said intravenous puncture tip, a second blunted tip adjacent said non-patient puncture tip, an activation mechanism for causing said axial displacement of said blunting member with respect to said intravenous puncture tip; and
   b) a needle holder attached to said needle assembly, said needle holder including an outer body having a first end adapted for attachment to said needle assembly and a second end having an internal opening therein, said needle holder further including an inner body slidable within said outer body and having opposite first and second ends, said first end of said inner body being slidably disposed within said outer body, said second end of said inner body including an internal opening for accommodating a blood collection tube therein, said inner body being configured for engagement with said activation member of said needle assembly for causing said axial displacement of said blunting member, the inner body and the outer body having locking elements that engage to prevent sliding movement of the inner body relevant to the outer body after the activation mechanism is in the second activated position.

9. A safety collection assembly as in claim 8, wherein said blunting member includes a first end comprising said first blunted tip and a second opposing end comprising said non-patient puncture tip and wherein axial displacement of said blunting member with respect to said intravenous puncture tip between said first retracted position and said second activated position also causes axial displacement of said non-patient puncture tip with respect to said second blunting tip between a first retracted position in which said non-patient puncture tip extends beyond said second blunted tip and a second activated position in which said second blunted tip extends beyond said non-patient puncture tip.

\* \* \* \* \*